United States Patent
Kawamura

(10) Patent No.: US 10,194,880 B2
(45) Date of Patent: Feb. 5, 2019

(54) BODY MOTION DISPLAY DEVICE AND BODY MOTION DISPLAY METHOD

(71) Applicant: FUJIFILM Corporation, Tokyo (JP)

(72) Inventor: Takahiro Kawamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 656 days.

(21) Appl. No.: 14/807,666

(22) Filed: Jul. 23, 2015

(65) Prior Publication Data

US 2015/0327828 A1 Nov. 19, 2015

Related U.S. Application Data

(63) Continuation of application No. PCT/JP2014/054787, filed on Feb. 27, 2014.

(30) Foreign Application Priority Data

Mar. 6, 2013 (JP) .................................. 2013-043671

(51) Int. Cl.
*A61B 6/00* (2006.01)
*G06T 7/20* (2017.01)
(Continued)

(52) U.S. Cl.
CPC ............ *A61B 6/5264* (2013.01); *A61B 6/461* (2013.01); *A61B 6/463* (2013.01); *A61B 6/467* (2013.01);
(Continued)

(58) Field of Classification Search
None
See application file for complete search history.

(56) References Cited

U.S. PATENT DOCUMENTS

| 7,899,229 B2 | 3/2011 | Luo et al. |
| 2009/0060311 A1* | 3/2009 | Mostafavi ............ A61B 6/4441 382/132 |

(Continued)

FOREIGN PATENT DOCUMENTS

| JP | 9-190534 A | 7/1997 |
| JP | 2006-376 A | 1/2006 |

(Continued)

OTHER PUBLICATIONS

International Search Report issued in PCT/JP2014/054787, dated May 27, 2014.
(Continued)

*Primary Examiner* — Hoon K Song
(74) *Attorney, Agent, or Firm* — Birch, Stewart, Kolasch & Birch, LLP

(57) ABSTRACT

Disclosed are a body motion display device and a body motion display method which efficiently performs operation for confirming the presence or absence of body motion included in a radiographic image. An index value calculation unit calculates an index value representing body motion based on the ratio between contrast of a high-frequency component and contrast of a low-frequency component in a radiographic image at an analysis point set by an analysis point setting unit. A display control unit selectively displays, on a display unit, at least one of a plurality of kinds of body motion information based on index values at a plurality of analysis points.

25 Claims, 13 Drawing Sheets

(51) Int. Cl.
  *G06T 7/00* (2017.01)
  *G16H 50/50* (2018.01)
  *G06F 19/00* (2018.01)

(52) U.S. Cl.
  CPC ............ *A61B 6/5211* (2013.01); *G06F 19/00* (2013.01); *G06T 7/00* (2013.01); *G06T 7/20* (2013.01); *G16H 50/50* (2018.01); *G06T 2207/10116* (2013.01); *G06T 2207/20016* (2013.01); *G06T 2207/30012* (2013.01); *G06T 2207/30168* (2013.01)

(56) References Cited

U.S. PATENT DOCUMENTS

| | | | | |
|---|---|---|---|---|
| 2010/0280355 | A1* | 11/2010 | Grimm | A61B 5/02028 600/411 |
| 2011/0082371 | A1* | 4/2011 | Chono | A61B 6/5217 600/443 |
| 2011/0123070 | A1* | 5/2011 | Sebok | G06T 7/74 382/132 |
| 2012/0059239 | A1 | 3/2012 | Yamaguchi | |
| 2012/0089016 | A1* | 4/2012 | Mizuno | G06T 11/206 600/425 |

FOREIGN PATENT DOCUMENTS

| | | |
|---|---|---|
| JP | 2006-421 A | 1/2006 |
| JP | 2006-34521 A | 2/2006 |
| JP | 2006-217939 A | 8/2006 |
| JP | 2011-247358 A | 12/2011 |
| JP | 2012-75862 A | 4/2012 |

OTHER PUBLICATIONS

Written Opinion of the International Searching Authority issued in PCT/JP2014/054787, dated May 27, 2014.
Japanese Notice of Reasons for Rejection dated Feb. 9, 2016, for Japanese Application No. 2013-043671 with the English translation.

\* cited by examiner

BODY MOTION DISPLAY DEVICE AND BODY MOTION DISPLAY METHOD

CROSS REFERENCE TO RELATED APPLICATIONS

This application is a Continuation of PCT International Application No. PCT/JP2014/054787 filed on Feb. 27, 2014 which claims priority under 35 U.S.C § 119(a) to Japanese Patent Application No. 2013-043671 filed on Mar. 6, 2013, all of which are hereby expressly incorporated by reference into the present application.

BACKGROUND OF THE INVENTION

1. Field of the invention

The present invention relates to a body motion display device and a body motion display method which display body motion of a subject at the time of photographing of a radiographic image.

2. Description of the Related Art

When photographing a subject by irradiating the subject with radiation, such as X-rays, to photograph the subject and acquiring a radiographic image of the subject, the acquired radiographic image may be blurred due to body motion caused by movement of the subject during photographing, and image quality may be deteriorated. In particular, when a photographing target is a region where the irradiation time of radiation is long, such as a neck, chest, abdomen, and waist, or when an infant is photographed, body motion is likely to occur, and thus, deterioration of the radiographic image becomes a problem.

A technician who performs photographing observes the condition of a subject during photographing and immediately confirms an acquired radiographic image, whereby the presence or absence of body motion can be determined. Meanwhile, a monitor in a photographing room has low resolution and displays a radiographic image on a reduced scale, and in many cases, an observation environment is comparatively bright. For this reason, it is difficult to determine the presence or absence of body motion by observing a displayed radiographic image. In this case, the presence or absence of body motion is determined by magnifying a radiographic image and confirming body motion of the entire radiographic image while moving the magnified region on the radiographic image. However, this operation degrades the workflow of the radiology technician who performs photographing.

For this reason, a method which automatically detects body motion based on a radiographic image and displays a detection result has been suggested. For example, a method has been suggested, in which deterioration of an edge in a radiographic image is learned as feature quantities in two directions of a vertical direction and a horizontal direction, a plurality of regions of interest are set on the radiographic image, an edge is extracted from each region of interest, a probability that body motion is included in the region of interest based on the learned feature quantities and the extracted edge is calculated, and it is determined whether or not a shift due to body motion occurs in the radiographic image based on the calculated probability for each region of interest (see U.S. Pat. No. 7,899,229B). According to the method described in U.S. Pat. No. 7,899,229B, the radiographic image and the frame of a region of interest are displayed in a superimposed manner, and a region of interest where body motion is included is indicated with a different color from other regions of interest, or the like, whereby the presence or absence of body motion is easily recognized. A numerical value representing the probability that body motion is included in the region of interest is additionally displayed. Furthermore, a selected region of interest is displayed next to the radiographic image on a magnified scale, whereby body motion is easily confirmed.

A method has also been suggested, in which the presence or absence of body motion is automatically determined, and when body motion is present, a radiographic image is displayed on a magnified scale by an instruction of a technician (see JP2006-000376A).

SUMMARY OF THE INVENTION

According to the method described in U.S. Pat. No. 7,899,229B, the presence or absence of body motion can be determined for each of a plurality of region of interest; however, even when body motion of the same magnitude occurs in the same direction in each region of interest, it is necessary to confirm all regions of interest, and thus, the operation for confirming the presence or absence of body motion is not efficient. According to the method described in JP2006-000376A, when body motion is present, the radiographic image is displayed on a magnified scale, and the technician must search for a portion in which body motion is present.

The invention has been accomplished in consideration of the above-described situation, and an object of the invention is to enable a more efficient operation for confirming the presence or absence of body motion in a radiographic image.

A body motion display device according to the invention includes an index value calculation part for calculating an index value representing the degree of body motion of a subject included in a radiographic image in a plurality of portions on the radiographic image, and a display control part for selectively displaying, on a display part, at least one of a plurality of kinds of body motion information based on the index values in the plurality of portions.

In the body motion display device according to the invention, in case where the body motion information is information representing the magnitude of the index value, the display control part may be part for selectively displaying, on the display part, at least one of the kinds of body motion information on the radiographic image in a superimposed manner.

In this case, the body motion information may be a mark whose color and/or shape is different according to the magnitude of the index value.

The body motion information may be a vector according to the magnitude and direction of the index value.

The display control part may display, on the display part, the number of kinds of body motion information according to the display characteristics of the display part.

The body motion information may include magnified images of the plurality of portions.

In this case, the display control part may change at least one of the display range of the magnified images and a magnification factor of the magnified image according to a region of the subject.

In this case, the display control part may change at least one of a display range of the magnified images and a magnification factor of the magnified images according to the display characteristics of the display part.

In this case, the display control part may display, on the display part, a reference image, which is referred to for the determination of the presence or absence of body motion, along with the body motion information.

In the body motion display device according to the invention, the display control part may display, on the display part, the body motion information for a portion in which an index value becoming a specific value is calculated.

A body motion display method according to the invention includes calculating an index value representing the degree of body motion of a subject included in a radiographic image in a plurality of portions on the radiographic image, and selectively displaying, on display part, at least one of a plurality of kinds of body motion information based on the index values in the plurality of portions.

There may be a provided a program which causes a computer to execute the body motion display method according to the invention.

According to the body motion display device and method of the invention, the index value representing the degree of body motion included in the radiographic image is calculated in the plurality of portions on the radiographic image, and at least one of the plurality of kinds of body motion information based on the index values in the plurality of portions is selectively displayed on the display part.

For this reason, the excessive display of the body motion information for a plurality of portions is suppressed, and as a result, it is possible to efficiently perform the operation for confirming the presence or absence of body motion.

DESCRIPTION OF THE PREFERRED EMBODIMENTS

Figure 1:
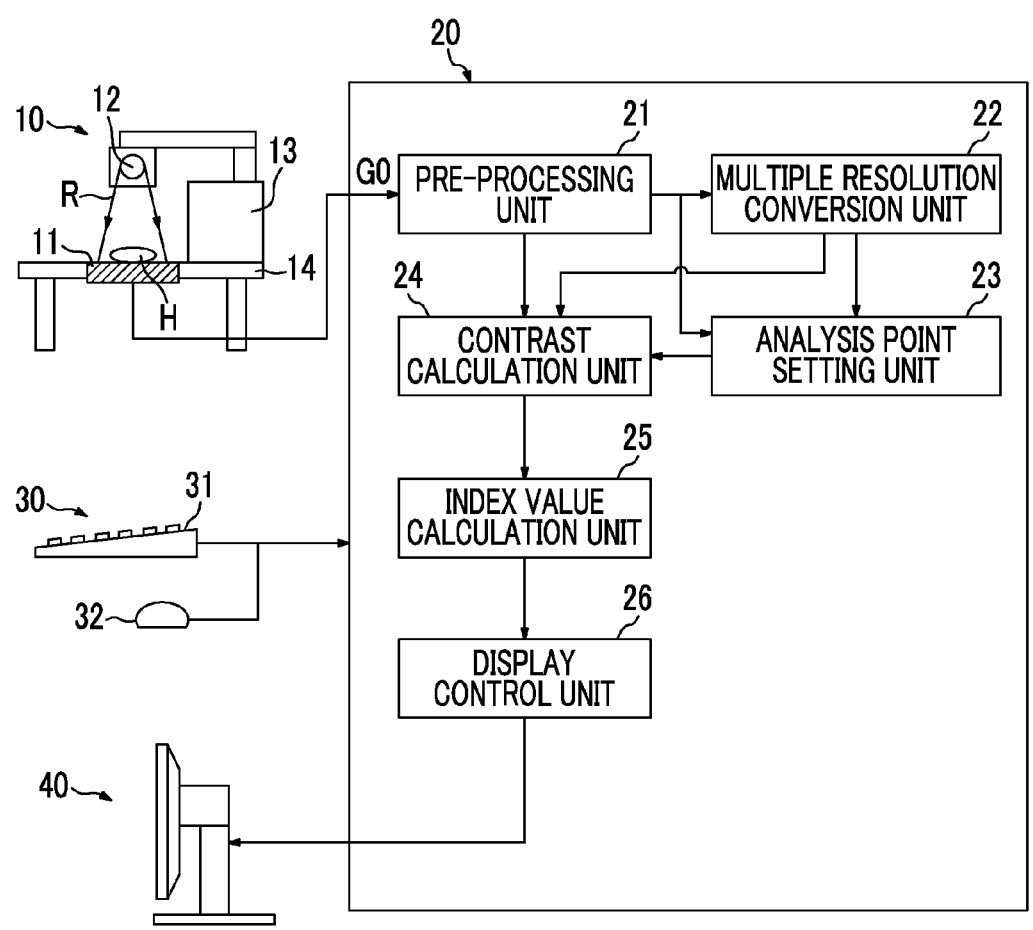
FIG. 1 is a schematic view showing the configuration of a radiographic image photographing system to which a body motion display device according to a first embodiment of the invention is applied.

Hereinafter, an embodiment of the invention will be described in detail referring to the drawings. FIG. 1 is a schematic view showing the configuration of a radiographic image photographing system to which a body motion display device according to a first embodiment of the invention is applied. The radiographic image photographing system of this embodiment includes a photographing apparatus 10 which photographs a subject to acquire a radiographic image G0 of the subject, a signal processing unit 20 which includes a body motion display device of the first embodiment, which detects body motion based on the radiographic image G0, an input unit 30 which gives various instructions to the signal processing unit 20, and a display unit 40 which displays the radiographic image acquired by photographing and the like.

The photographing apparatus 10 includes a radiation tube bulb 12 which irradiates a subject H with radiation R, a photographing control unit 13 which controls driving of the radiation tube bulb 12, and a photographing stand 14 on which the subject H is placed. The photographing stand 14 is provided with a radiation detector 11 which outputs a radiation detection signal of the subject H. The radiation detector 11 outputs a radiation detection signal corresponding to an energy level of irradiated radiation for each of pixels arranged in a matrix, and the detection signal is subjected to A/D conversion processing and is output as a digital image signal representing the radiographic image G0 of the subject H.

As the radiation detector 11, for example, as described in JP1995-072253A (JP-H07-072253A), a radiation detector in which a scintillator configured to receive irradiation of radiation and to emit visible light and a solid-state photo detection element configured to detect visible light are laminated, or as described in JP2010-206067A, a radiation detector which has a radiation photo-conductive layer configured to receive irradiation of radiation and to output an electrical signal corresponding to energy of radiation can be applied.

The signal processing unit 20 includes a pre-processing unit 21 to which the digital image signal representing the radiographic image G0 is input, a multiple resolution conversion unit 22, an analysis point setting unit 23, a contrast calculation unit 24, an index value calculation unit 25, and a display control unit 26. The index value calculation unit 25 and the display control unit 26 constitute the body motion display device.

The input unit 30 is constituted by, for example, a keyboard 31, a mouse 32, and the like, and inputs various instructions of a user, such as a radiology technician, to the signal processing unit 20.

The display unit 40 is constituted by, for example, a liquid crystal display, a CRT display, or the like, and displays body motion information relating to movement of the subject H, a determination result of the presence or absence of body motion, a photographed radiographic image of the subject, and the like as necessary.

The signal processing unit 20, the input unit 30, and the display unit 40 described above can be constituted by, for example, a computer system, such as a general personal computer.

Next, photographing of a radiographic image will be described. At the time of photographing of a radiographic image, the radiation detector 11 is placed on the photographing stand 14 of the photographing apparatus 10, and the subject H is placed on the radiation detector 11. In this state, the photographing control unit 13 is operated, whereby the radiation tube bulb 12 is driven, radiation R is transmitted through the subject H, and the radiation detector 11 is irradiated with the radiation R. If photographing ends, the digital image signal representing the radiographic image G0 is acquired from the radiation detector 11. The radiographic image G0 can be reproduced and displayed on the display unit 40.

Figure 2:
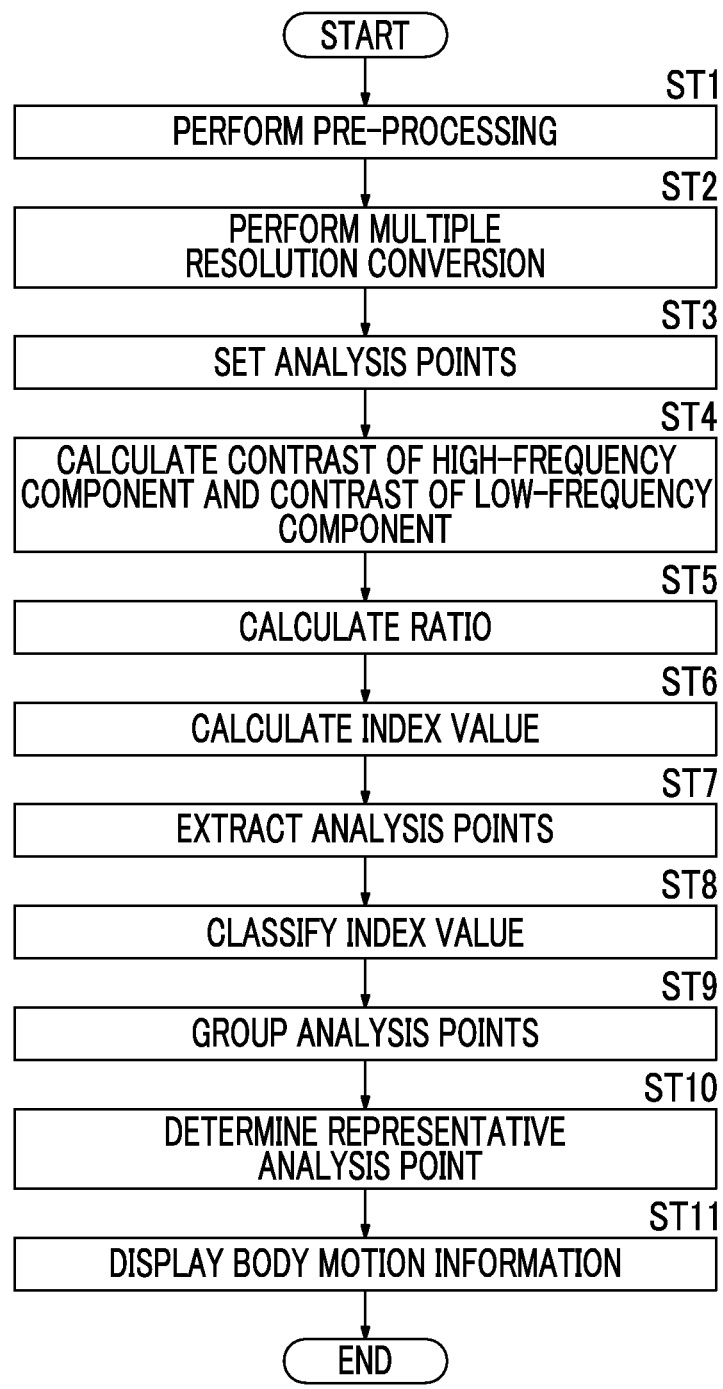
FIG. 2 is a flowchart showing processing which is performed in a signal processing unit.

The radiographic image G0 is input to the signal processing unit 20. Hereinafter, processing which is performed in the signal processing unit 20 will be described. FIG. 2 is a flowchart showing processing which is performed in the signal processing unit 20. The radiographic image G0 input to the signal processing unit 20 is first subjected to processing for correcting fluctuation in a signal value due to irradiation irregularity of radiation and detection irregularity of the radiation detector 11, image processing for correcting a concentration, contrast, a frequency component, and the like to improve image quality of the radiographic image G0, and other kinds of appropriate processing as necessary in the pre-processing unit 21 (pre-processing, Step ST1).

Figure 3:
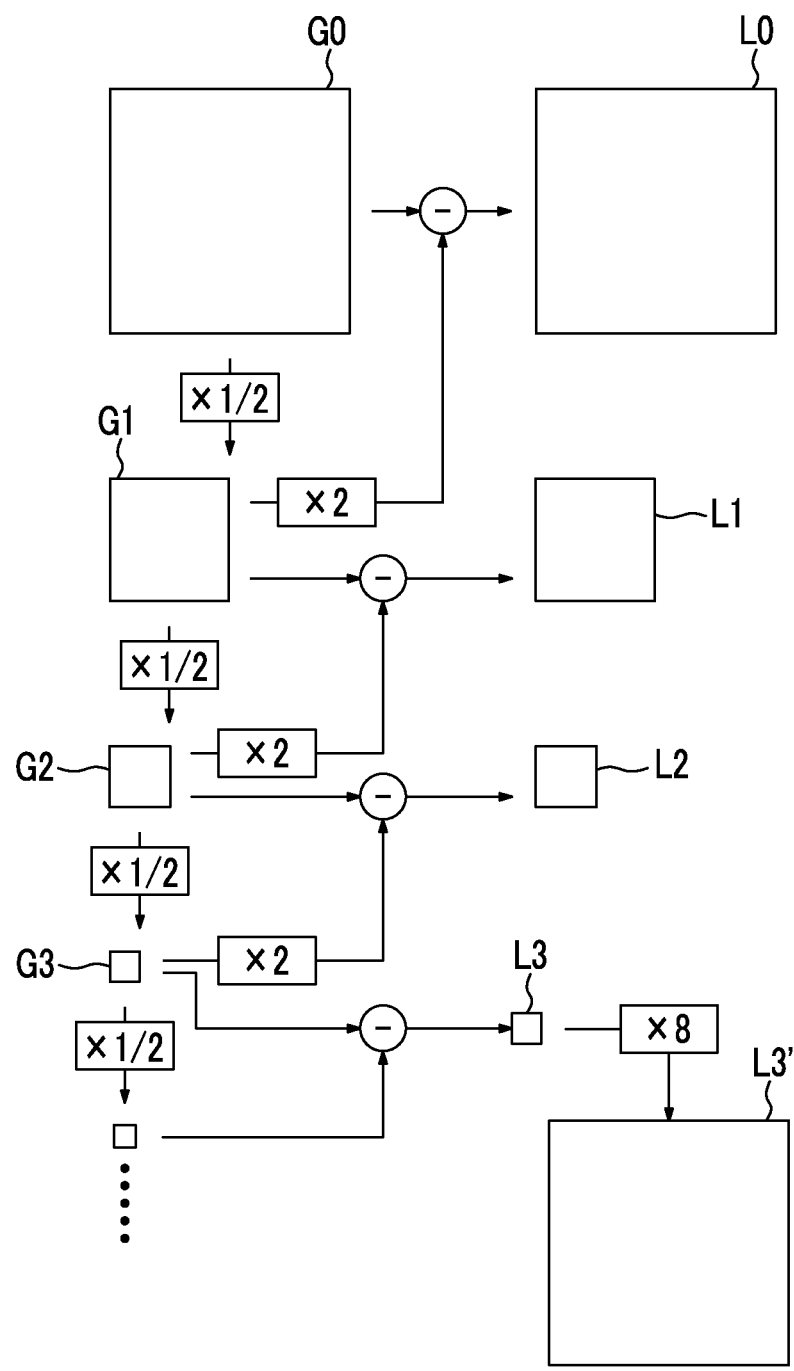
FIG. 3 is a diagram illustrating multiple resolution conversion.

Next, the multiple resolution conversion unit 22 performs multiple resolution conversion of the radiographic image G0 subjected to the pre-processing, and extracts a high-frequency component and a low-frequency component of the radiographic image G0 (Step ST2). FIG. 3 is a diagram illustrating multiple resolution conversion. First, the multiple resolution conversion unit 22 performs filtering processing on the radiographic image G0 using a Gaussian filter of $\sigma=1$, and reduces the radiographic image G0 to ½ to generate a Gaussian component G1. The Gaussian component G1 is obtained by reducing the radiographic image G0 to ½. Next, the multiple resolution conversion unit 22 performs an interpolation operation, such as third order B spline interpolation, to magnify the Gaussian component G1 to the same size as the radiographic image G0, and subtracts the magnified Gaussian component G1 from the radiographic image G0 to generate a Laplacian component L0 of the highest frequency band. In this embodiment, the Laplacian component L0 is used as a high-frequency component. In this embodiment, for convenience, the highest frequency band is called a zero-th frequency band.

Next, the multiple resolution conversion unit 22 performs filtering processing on the Gaussian component G1 using the Gaussian filter of $\sigma=1$, and further reduces the Gaussian component G1 to ½ to generate a Gaussian component G2. The Gaussian component G2 is magnified to the same size as the Gaussian component G1, and subtracts the magnified Gaussian component G2 from the Gaussian component G1 to generate a Laplacian component L1 of a first frequency band. The above-described processing is repeated until a Laplacian component of a desired frequency band is generated, whereby Laplacian components Lj (where j=0 to n) of a plurality of frequency bands are generated.

In this embodiment, the above-described processing is repeated until a Laplacian component L3 of a third frequency band is obtained, and the Laplacian component L3 is magnified eight times so as to have the same size as the Laplacian component L0 of the first frequency band to generate a Laplacian component L3'. The Laplacian component L3' is used as a low-frequency component.

The signal value of each pixel of the Gaussian component represents the concentration of the pixel, and the signal value of each pixel of the Laplacian component represents the magnitude of a frequency component of the frequency band in the pixel.

With the use of other methods of multiple resolution conversion, such as wavelet conversion, a plurality of band images having different frequency bands may be generated, the band image of the highest frequency band may be used as a high-frequency component, and an image obtained by magnifying the band image of the third frequency band the same as described above eight times may be used as a low-frequency component. The frequency band of the low-frequency component is not limited to the third frequency band, and a frequency component of an arbitrary frequency band can be used as a low-frequency component as long as the frequency band is lower than the highest frequency band. As the high-frequency component, the radiographic image G0 itself may be used.

Figure 4:
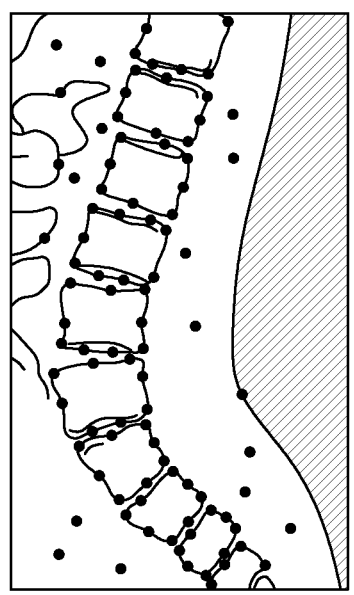
FIG. 4 is a diagram showing an example of set analysis points.

Next, the analysis point setting unit 23 sets analysis points for calculating contrast described below on the radiographic image G0 subjected to the pre-processing (Step ST3). Specifically, analysis points are set using the low-frequency component L3'. Hereinafter, the setting of the analysis points will be described. The analysis point setting unit 23 extracts a subject region from the radiographic image G0 so as to limit a target of detection of body motion to a subject of the subject including the bone included in the radiographic image G0 by excluding the influence of scan lines or an irradiation field frame included in the radiographic image G0. Specifically, the subject region is extracted from the radiographic image G0 using various segmentation techniques, such as a method using a learning result on a target subject, a method of a rule base on the subject, and a graph cut method. It is preferable that the analysis points are extracted on portions in which the presence or absence of body motion is easily determined, specifically, on the edge of the bone. For this reason, the analysis point setting unit 23 sets pixels having a comparatively high pixel value from a subject region A0 in the low-frequency component L3' generated by the multiple resolution conversion unit 22 as analysis points. Examples of the analysis points set in this manner are shown in FIG. 4.

Figure 5:
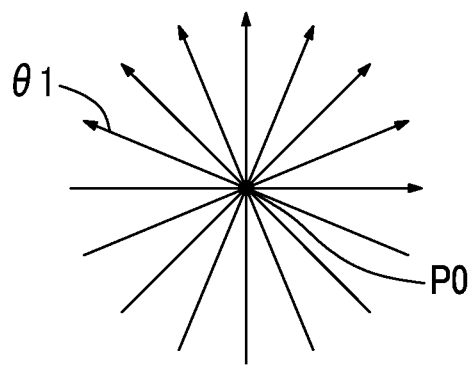
FIG. 5 is a diagram illustrating eight directions centering on an analysis point.

Next, the contrast calculation unit 24 calculates contrast of the high-frequency component and contrast of the low-frequency component at the analysis points (Step ST4). For a short period of time (tens of milliseconds to hundreds of milliseconds) during which the subject is irradiated with radiation, body motion appears as a shift in one direction. When body motion occurs, the radiographic image G0 is deteriorates in the same direction as the direction of body motion, but is not deteriorated in a direction perpendicular to the direction of body motion. For this reason, the contrast calculation unit 24 first calculates the gradient direction of the edge at each analysis point. Specifically, as shown in FIG. 5, the contrast calculation unit 24 sets eight directions centering on an analysis point P0 on the low-frequency component L3'. For example, when the direction from the bottom toward the top of the paper is used as a reference (0 degrees), eight directions of −67.5 degrees, −45 degrees, −22.5 degrees, 0 degrees, 22.5 degrees, 45 degrees, 67.5 degrees, and 90 degrees are set. The eight directions are respectively referred to as θ1 to θ8. The number of directions to be set is not limited to eight, and an arbitrary number of directions, such as two directions, four directions, or 16 directions, may be set.

An analysis region of a specific size centering on the analysis point P0 is set in each direction. The analysis region is, for example, a rectangular region of 9×9 pixels. A plurality of lines in the analysis region are virtually set, and the difference value between the maximum value and the minimum value of the pixel value in each line is calculated as contrast in each line. The direction of the line matches the direction in which the analysis region is set. For example, when an analysis region is set in the direction θ1 shown in FIG. 5, the direction of a line set in the analysis region becomes θ1.

Figure 6:
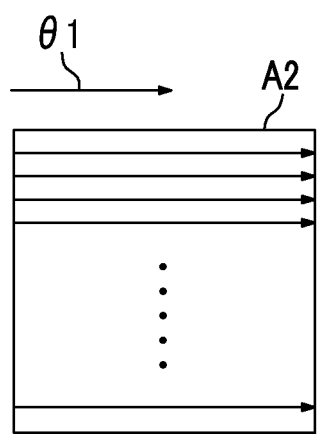
FIG. 6 is a diagram illustrating an analysis region and lines in a horizontal direction.

FIG. 6 is a diagram illustrating an analysis region and lines in a horizontal direction. As shown in FIG. 6, a plurality of lines are set in an analysis region A2 in a certain direction θ1 of an analysis point P0. The number of lines may be the same as the number of pixels in a vertical direction of the analysis region A2. That is, if the size of the analysis region A2 is 9×9 pixels, the number of lines may be nine. The number of lines may be appropriately decreased.

The contrast calculation unit 24 calculates an average value of contrast on all lines as contrast on the direction, in which the analysis region is set, in the low-frequency component L3'. The contrast calculation unit 24 calculates an average value of contrast on each of the analysis regions set in all of the eight directions θ1 to θ8 as contrast CLθi (where i=1 to 8) on each analysis region. The contrast calculation unit 24 determines the direction, in which the analysis region where contrast having the highest value among the calculated eight values of contrast CLθi is calculated is set, as the gradient direction of the edge on the analysis point.

The contrast calculation unit 24 calculates eight kinds of contrast CHθi (where i=1 to 8) on all of the eight directions θ1 to θ8 at all analysis points on the high-frequency component L0, like the low-frequency component L3'. The contrast calculation unit 24 determines the direction, in which the analysis region where contrast having the highest value among the calculated eight values of contrast CHθi is calculated is set, as the gradient direction of the edge on the analysis point.

Since the direction in which contrast changes at each analysis point is the same between the low-frequency component L3' and the high-frequency component L0, the edge gradient directions at the respective analysis points match each other. For this reason, one kind of contrast CHθi of the high-frequency component and one kind of contrast CLθi of the low-frequency component on the same edge gradient direction at each analysis point are calculated.

When body motion occurs during photographing, contrast of the high-frequency component in the acquired radiographic image G0 is degraded, but contrast of the low-frequency component is not degraded. While contrast of the entire radiographic image changes according to photographing conditions or the type of the subject, the change appears as the difference in contrast of the low-frequency component. Therefore, the ratio between contrast of the high-frequency component and contrast of the low-frequency component can be used as an index value representing the degree of body motion.

For this reason, the index value calculation unit 25 calculates the ratio between contrast CHθi of the high-frequency component and contrast CLθi of the low-frequency component at each analysis point, specifically, the ratio CRθi (CRθi=CHθi/CLθi) of contrast CHθi of the high-frequency component to contrast CLθi of the low-frequency component (Step ST5). The index value calculation unit 25 calculates an average value CRmθi of the ratio CRθi in each direction θi and calculates the lowest average value CRmθi as an index value representing the degree of body motion (Step ST6).

The calculation of the index value representing the degree of body motion is not limited to the above-described method, and the ratio CRθi between contrast CHθi of the high-frequency component and contrast CLθi of the low-frequency component on all of the eight directions at each analysis point may be calculated, an average value CRmθi of the ratio CRθi between contrast CHθi of the high-frequency component and contrast CLθi of the low-frequency component on all analysis points in each direction θi may be calculated, and the lowest average value CRmL among the average values may be calculated as an index value representing the degree of body motion.

The display control unit 26 selectively displays, on the display unit 40, at least one of a plurality of kinds of body motion information based on the index values at a plurality of analysis points. Hereinafter, the selective display of the body motion information will be described.

As described above, when body motion occurs during photographing, contrast of the high-frequency component in the acquired radiographic image G0 is degraded, but contrast of the low-frequency component is not degraded. For this reason, when body motion does not occur, the index value becomes a value close to 1; however, when body motion occurs, the index value is smaller than 1, and becomes a smaller value when body motion is larger. For this reason, the display control unit 26 first compares the index value at each analysis point with a threshold value Th1, and extracts analysis points, at which the index value is less than the threshold value Th1, among a plurality of analysis points (Step ST7). The threshold value Th1 is a prescribed value smaller than 1.

Figure 7:
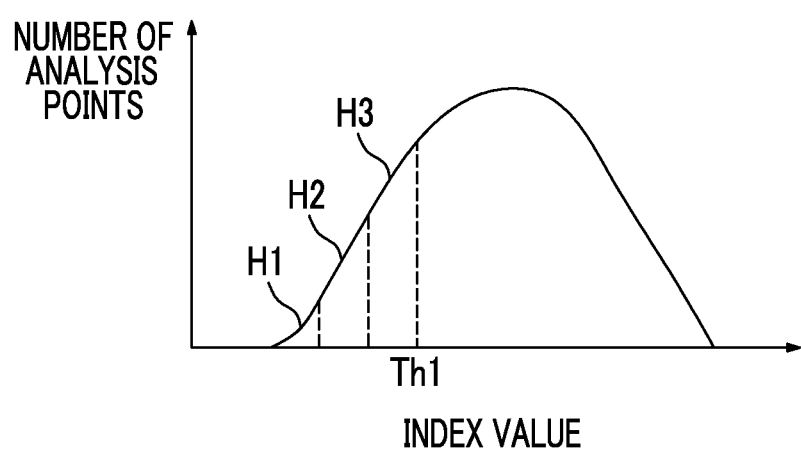
FIG. 7 is a diagram showing a histogram in which the horizontal axis is plotted in terms of an index value and the vertical axis is plotted in terms of the number of analysis points.

The display control unit 26 classifies the magnitude of the index value in a plurality of stages on the extracted analysis points (Step ST8). In this embodiment, the magnitude of the index value is classified in three stages, but the number of classifications is not limited thereto. FIG. 7 is a diagram showing a histogram in which the horizontal axis is plotted in terms of an index value and the vertical axis is plotted in terms of the number of analysis points. As shown in FIG. 7, the display control unit 26 further classifies portions, in which the index value is less than the threshold value Th1, into three regions H1 to H3. In the regions H1 to H3, body motion is larger when the index value is smaller. For this reason, when displaying the radiographic image G0 on the display unit 40, the display control unit 26 displays marks in different colors according to the magnitude of the index values as body motion information on the analysis points classified in the regions H1 to H3. For example, marks of red, blue, and white are displayed in an ascending order of the index values, that is, in a descending order of the magnitude of body motion.

Figure 8:
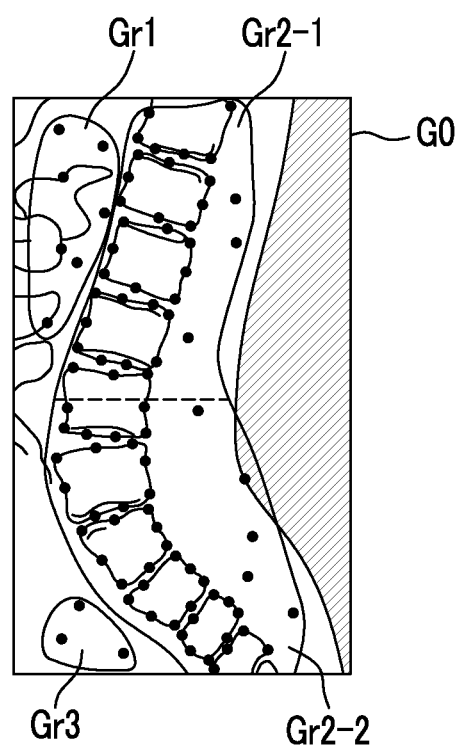
FIG. 8 is a diagram showing a result of grouping of analysis points.

The display control unit 26 confirms the direction and magnitude (that is, the magnitude of the index value) of body motion at each analysis point, and groups analysis points at which the direction and magnitude of body motion are the same between adjacent analysis points (Step ST9). FIG. 8 is a diagram showing a result of grouping. In FIG. 8, it is assumed that a plurality of analysis points are grouped into three groups Gr1 to Gr3.

The display control unit 26 determines a representative analysis point which represents each of the groups Gr1 to Gr3 (Step ST10). Since the group Gr2 includes a very large number of analysis points, it is assumed that the analysis points are appropriately divided into a plurality of groups (in this case, two groups Gr2-1 and Gr2-2), and one representative analysis point in each of the groups Gr2-1 and Gr2-2 is determined. The representative analysis point may be, for example, an analysis point located at the most center of each of the groups Gr1 to Gr3.

Figure 9:
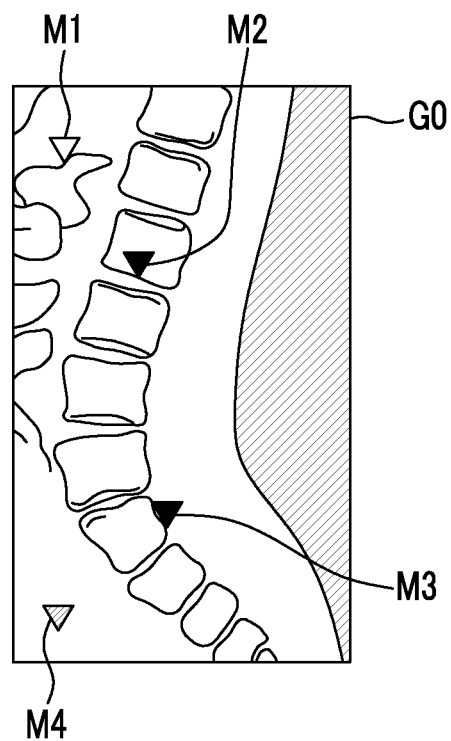
FIG. 9 is a diagram showing a state where marks as body motion information are displayed on a radiographic image.

The display control unit 26 displays a mark (that is, body motion information) at the position of the representative analysis point of each of the groups Gr1 to Gr3 on the radiographic image G0 (Step ST11), and ends the processing. FIG. 9 is a diagram showing the radiographic image G0 on which marks are displayed. While a subject region A0 in the radiographic image G0 is displayed on the display unit 0, in the following description, description will be provided assuming that the radiographic image G0 is displayed. As shown in FIG. 9, triangular marks M1 to M4 having different colors are displayed at the representative analysis points of the groups Gr1, Gr2-1, Gr2-2, and Gr3. In FIG. 9, different colors are represented by changing the form of filling of the triangle. The shape of the mark may be changed according to the magnitude of the index value, instead of color, or the shape of the mark may be changed along with color.

In this way, in the first embodiment, since at least one of a plurality of kinds of body motion information based on the index values is selectively displayed on the display unit 40, all kinds of body motion information on a plurality of analysis point are prevented from being displayed, and as a result, it is possible to efficiently perform the operation for confirming the presence or absence of body motion.

Since the body motion information is a mark whose color is different according to the magnitude of the index value, a portion which should be carefully observed due to the presence of body motion is easily selected based on the difference in color.

Since the body motion information on the analysis points, at which the index value is less than the threshold value Th1, are displayed, it is possible to easily specify a portion in which body motion is present and which should be carefully observed.

In the first embodiment, although the analysis points at which the direction and magnitude of body motion are the same are grouped, and the body motion information is displayed at the position of the representative analysis point of each group, a representative analysis point may be determined based on the distance between adjacent analysis points and the similarity of the direction and magnitude of body motion between adjacent analysis points. For example, when the similarity of the direction and magnitude of body motion is equal to or greater than predetermined similarity on a certain analysis point and another analysis point closest to the analysis point, it is determined that the two analysis points belong to the same group, one analysis point remains, and the other analysis point is deleted. This operation may be repeatedly performed on all analysis points, the final remaining analysis point may be determined as a representative analysis point of a group of analysis points at which the direction and magnitude of body motion are similar, and the direction and magnitude of body motion may be displayed at the position of the representative analysis point.

Figure 10:
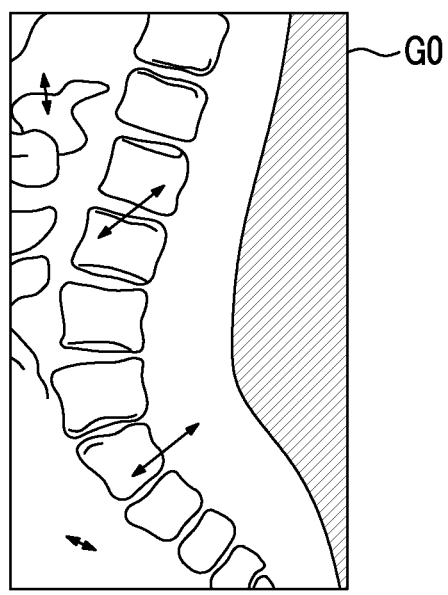
FIG. 10 is a diagram showing a state where vectors as body motion information are displayed on a radiographic image.

In the first embodiment, as shown in FIG. 10, a vector according to the magnitude and direction of body motion may be displayed on the radiographic image G0 as body motion information, instead of marks. In FIG. 10, although the magnitude of a vector is different according to the magnitude of the index value, at least one of the thickness, line type, and color of the vector may be changed according to the magnitude of body motion. With this, it is possible to easily estimate the cause of body motion, and as a result, it is possible to easily take measures, such as fixing a portion in which body motion occurs, when performing re-photographing.

There is a number of kinds of body motion information to be displayed optimal for confirming the radiographic image G0 according to the display characteristics of the display unit 40, specifically, according to the resolution, display luminance, display range, and the like of the display unit 40. For example, when the resolution of the display unit 40 is low, if a large number of kinds of body motion information are displayed, body motion is not easily confirmed. For this reason, the number of kinds of body motion information according to the display characteristics of the display unit 40 is displayed, whereby it is possible to easily confirm body motion.

In the first embodiment, although the mark or the like representing the magnitude of the index value is displayed as the body motion information, a magnified image obtained by magnifying a region centering on an analysis point may be displayed as body motion information. Hereinafter, this case will be described as a second embodiment.

Figure 11:
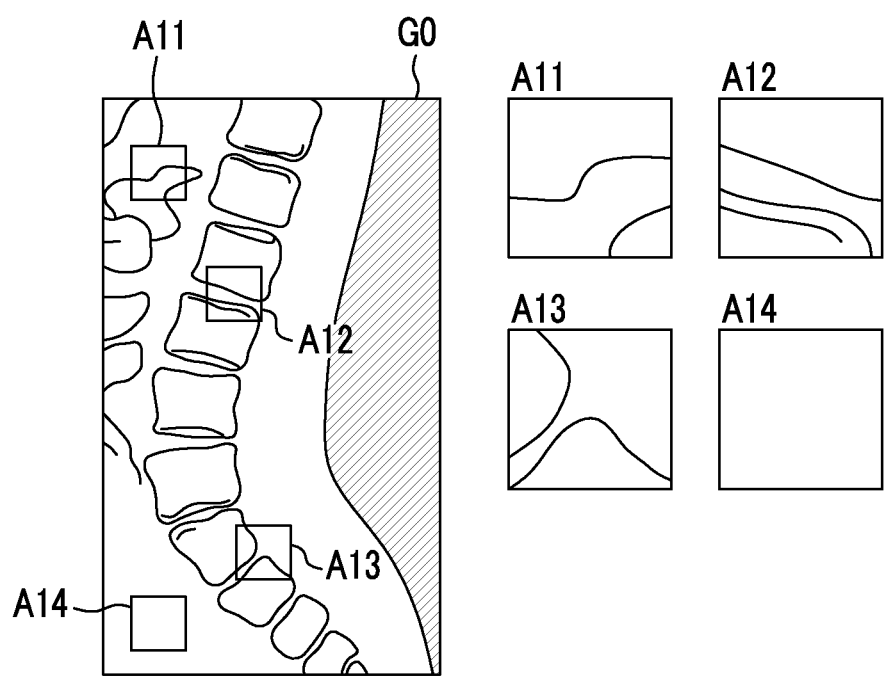
FIG. 11 is a diagram showing a state where magnified images as body motion information are displayed on a radiographic image.

An analysis point at which a magnified image is displayed is determined in the same manner as in the first embodiment. That is, analysis points at which body motion is in the same direction are grouped, and a representative analysis point which represents each group is determined. A region of a size centering on the representative analysis point is set on the radiographic image G0, and a magnified image of each region is displayed in parallel with the radiographic image G0. FIG. 11 is a diagram illustrating the display of body motion information in the second embodiment. As shown in FIG. 11, on four analysis points, rectangular regions A11 to A14 centering on the respective analysis points are set. The magnified images of the regions A11 to A14 are displayed in parallel with the radiographic image G0 as body motion information. It is preferable that the size of a magnified image is about ¼ to ½ of a screen size in the display unit 40. Not only a plurality of magnified images may be displayed in parallel, but also a plurality of magnified image may be displayed so as to be sequentially switchable.

As in the second embodiment, when the magnified image is displayed as the body motion information, the display range and magnification factor of the magnified image suitable for confirming body motion are different according to the region of the subject H to be displayed. For this reason, at least one of the display range and the magnification factor of the magnified image may be changed according to the display characteristics of the display unit 40. With this, it is possible to more easily confirm body motion using the magnified image. For example, when a region to be observed is the bone of the subject H, ease of recognition of the edge becomes more important. For this reason, when observing the bone, the bone is displayed larger compared to a case of observing a soft tissue or the like, thereby easily confirming body motion of the bone.

The display range and the magnification factor of the magnified image suitable for confirming body motion are different according to the display characteristics of the display unit 40. For this reason, at least one of the display range and the magnification factor of the magnified image may be changed according to the display characteristics of the display unit 40. With this, it is possible to more easily confirm body motion using the magnified image.

Figure 12:
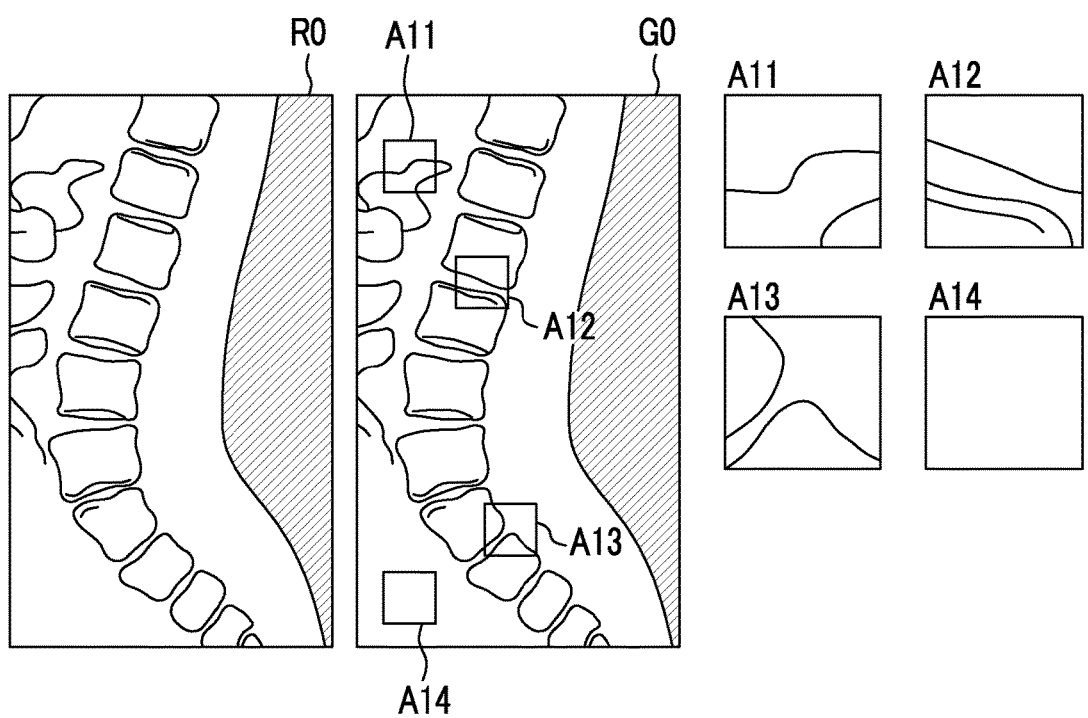
FIG. 12 is a diagram showing a state where a radiographic image, magnified images of the radiographic image, and a reference image are displayed in parallel.

While a skilled radiology technician comparatively easily determines the presence or absence of body motion while viewing the magnified image, in many cases, it is difficult for an inexperienced technician to determine the presence or absence of body motion. For this reason, a reference image for determining the presence or absence of body motion and body motion information may be displayed in parallel. Specifically, the radiographic image G0 on which the presence or absence of body motion is confirmed and the index value on the radiographic image G0 are stored in a database connected to the radiographic image photographing system or provided in the system, and a radiographic image, which has an index value comparatively close to the index value calculated on the target radiographic image G0, among the radiographic images of the same region previously photographed on the radiographic image G0 subject to the confirmation of the presence or absence of body motion is set as a reference image. The reference image is displayed on the display unit 40 in parallel with the target radiographic image G0 when displaying the magnified image as the body motion information as in the second embodiment. FIG. 12 is a diagram showing a state where the radiographic image G0, magnified images of the radiographic image G0, and a reference image are displayed in parallel. As shown in FIG. 12, a reference image R0 is displayed in parallel with the radiographic image G0 and the magnified images, whereby it is possible to easily confirm whether or not body motion is included in a magnified image using the reference image R0, and thus, to more efficiently perform the operation for confirming the presence or absence of body motion.

As the reference image R0, not only a radiographic image which has an index value comparatively close to the index value calculated on the target radiographic image G0, but also a radiographic image in which it is determined that body motion is absent may be used as the reference image R0. In this case, it is possible to easily confirm whether or not body motion is included in a magnified image with reference to the reference image R0, and thus, to more efficiently perform the operation for confirming the presence or absence of body motion.

Figure 13:
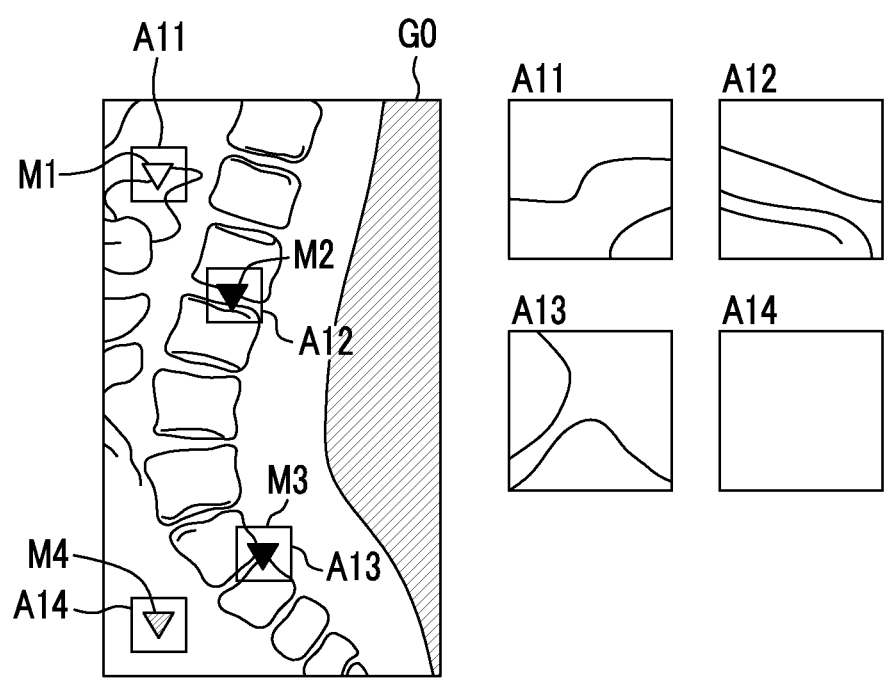
FIG. 13 is a diagram showing a state where marks and magnified images as body motion information are displayed on a radiographic image.

Although in the first embodiment, the mark or the like representing the magnitude of the index value is displayed as the body motion information, and in the second embodiment, the magnified image is displayed as the body motion information, both the mark or the like representing the magnitude of the index value and the magnified image may be displayed as the body motion information. Hereinafter, this case will be described as a third embodiment. FIG. 13 is a diagram showing a state where both marks and magnified images are displayed. As shown in FIG. 13, in the third embodiment, marks M1 to M4 are displayed on the radiographic image G0 as in the first embodiment, and magnified images of regions A11 to A14 centering on analysis points assigned with the marks M1 to M4 are displayed in parallel with the radiographic image G0. With this, it is possible to more easily confirm the presence or absence of body motion.

In the first to third embodiments, after the presence or absence of body motion is confirmed, when it is determined that "body motion is present", it is necessary to re-photograph the subject H. When performing re-photographing, it is preferable to change the photographing conditions at the time of re-photographing according to the degree of body motion. For example, when body motion occurs, the irradiation time of radiation at the time of re-photographing is set to be short, whereby the influence of body motion can be reduced. For example, when body motion occurs at the time of initial photographing under the photographing conditions that a tube current is 100 mA and the irradiation time of radiation is 150 msec, at the time re-photographing, the photographing conditions with a shorter irradiation time, such as the photographing conditions that the tube current is 300 mA and the irradiation time is 50 msec, are set. With this, it is possible to reduce the influence of body motion at the time of re-photographing.

After the presence or absence of body motion is confirmed, when it is determined that "body motion is present", the user recognizes a place where body motion occurs. For this reason, re-photographing may be performed after the occurrence of body motion is prevented by fixing the place where body motion occurs or the like.

In the first to third embodiments, although the body motion information is selectively displayed only at the analysis points at which the index value is less than the threshold value Th1, the body motion information may be selectively displayed for all analysis points.

In the first to third embodiment, although the analysis point setting unit 23 sets a plurality of analysis points for determining the presence or absence of body motion, the radiographic image G0 may be displayed on the display unit 40, and the user may set a plurality of analysis points by a manual operation. The analysis points may be fixed positions on the radiographic image G0. In this case, a plurality of kinds of body motion information are selectively displayed at a plurality of analysis points, whereby it is possible to easily perform the operation for confirming the presence or absence of body motion.

In the first to third embodiments, although the index value is calculated based on the ratio between contrast $CH\theta i$ of the high-frequency component and contrast $CL\theta i$ of the low-frequency component at each analysis point, the index value is not limited thereto as long as the presence or absence of body motion can be recognized with the index value, and various known index values can be used. For example, a probability of body motion in a region of interest may be calculated using the method described in U.S. Pat. No. 7,899,229B, and the calculated probability may be used as an index value. In this case, body motion is larger when the index value is larger.

In the first to third embodiments, although the body motion information is selectively displayed at the four analysis points from among a plurality of analysis points on the radiographic image G0, the number of analysis points at which the body motion information is displayed is not limited thereto, and the body motion information may be displayed at an arbitrary number of analysis points. It is preferable that the number of kinds of body motion information to be displayed is about 5 to 20; however, as described above, it is preferable to appropriately increase or decrease the number of kinds of body motion information to be displayed according to the display characteristics of the display unit 40.

In the first to third embodiments, although a plurality of analysis points are set and the index value representing the degree of body motion is calculated, a plurality of regions may be set on the radiographic image G0, instead of the analysis points, and the index value representing the degree of body motion may be calculated for each region.

In the first to third embodiments, although the multiple resolution conversion unit 22 performs the multiple resolution conversion of the radiographic image G0 and acquires the high-frequency component and the low-frequency component of the radiographic image G0, a radiographic image G0 of a region in a predetermined range including an analysis point may be subjected to Fourier transform, a power spectrum on the analysis point may be obtained, and the value of a high frequency band and the value of a low frequency band predefined in the power spectrum may be calculated as contrast of a high-frequency component and contrast of a low-frequency component at the analysis point. In this case, the ratio between contrast of the high-frequency component and contrast of the low-frequency component substantially becomes the ratio between the high-frequency component and the low-frequency component in the power spectrum.

In the first to third embodiments, although body motion is determined using the radiographic image acquired in the photographing apparatus 10 which photographs the radiographic image of the subject using the radiation detector 11, the invention can be applied to when radiographic image information of the subject is accumulated and recorded in an accumulative phosphor sheet as a radiation detector shown in JP1996-266529A (JP-H08-266529A), JP1997-024039A (JP-09-024039A), and body motion is determined using a radiographic image acquired by photoelectrically reading the accumulative phosphor sheet.

As described above, when the radiographic image and the index value of the radiographic image are stored in the database, it is possible to confirm how much body motion occurs according to the photographing region of the subject H with reference to the database. For this reason, it is possible to confirm whether or not the photographing region is a region where body motion is likely to occur with reference to the database at the time of photographing, and when photographing the region where body motion is likely occur, to make body motion hard to occur by fixing the region where body motion is likely to occur or by making the irradiation time of radiation short.

Hereinafter, the functional effects of the preferred embodiment of the invention will be described.

When the body motion information is information representing the magnitude of the index value, at least one of the kinds of body motion information is displayed on the radiographic image in a superimposed manner, whereby it is possible to efficiently confirm the magnitude of body motion.

The body motion information is a mark whose color is different according to the magnitude of the index value, whereby a portion which should be carefully observed due to the presence of body motion is easily selected based on the difference in color.

The body motion information is a vector according to the magnitude and direction of the index value, whereby it is possible to easily estimate the cause of body motion, and as a result, it is possible to easily take measures, such as fixing a portion in which body motion is present, when performing re-photographing.

The body motion information on a portion in which an index value is equal to or greater than a specific value is displayed, whereby it is possible to easily specify a portion which should be carefully observed due to the presence of body motion.

There is a number of kinds of body motion information to be displayed optimal for confirming an image according to the display characteristics of the display part, specifically, the resolution, display luminance, display range, and the like. For example, in the display part having low resolution, if a large number of kinds of body motion information are displayed, body motion is not easily confirmed. For this reason, the number of kinds of body motion information according to the display characteristics of the display part are displayed, whereby it is possible to more easily confirm body motion.

When the body motion information is the magnified images of a plurality of portions, at least one of the kinds of body motion information is selectively displayed, whereby it is possible to efficiently confirm the magnitude of body motion.

The display range and the magnification factor of the magnified image suitable for confirming body motion are different according to the region of the subject. For this reason, at least one of the display range and the magnification factor of the magnified image is changed according to the display characteristics of the display part, whereby it is possible to more easily confirm body motion.

The display range and the magnification factor of the magnified image suitable for confirming body motion are different according to the display characteristics of the display part, specifically, the resolution, display luminance, display range, and the like. For this reason, at least one of the display range and the magnification factor of the magnified image is changed according to the display characteristics of the display part, whereby it is possible to more easily confirm body motion.

The reference image including body motion is displayed along with the body motion information, whereby it is possible to easily confirm whether or not body motion is included in the magnified image using the reference image, and thus, to efficiently perform the operation for confirming the presence or absence of body motion.

What is claimed is:

1. A body motion display device comprising:
an index value calculation part for calculating an index value representing the degree of body motion of a subject included in a radiographic image in a plurality of portions on the radiographic image; and
a display control part for selectively displaying, on display part, at least one of a plurality of kinds of body motion information based on index values calculated by the index value calculation part in the plurality of portions,
wherein the index value calculation part calculates a direction and a magnitude of the body motion of the subject included in the radiographic image as the index value at a plurality of analysis points on the radiographic image,
the body motion display device further comprising:
an analysis point setting unit for setting, in a case where the similarity of the direction and magnitude of body motion is equal to or greater than predetermined similarity on a certain analysis point of the plurality of analysis points and another analysis point closest to the analysis point, an operation of deleting one analysis points is performed, the operation is repeatedly performed on all analysis points, an analysis point finally remained as a representative analysis point of a group of analysis points at which the direction and the magnitude of the body motion are similar.

2. The body motion display device according to claim 1, wherein, in case where the body motion information is information representing the magnitude of the index value, the display control part selectively displays, on the display part, at least one of the body motion information on the radiographic image in a superimposed manner.

3. The body motion display device according to claim 2, wherein the body motion information is a mark whose at least one of a color and a shape is different according to the magnitude of the index value.

4. The body motion display device according to claim 2, wherein the body motion information is a vector according to the magnitude and direction of the index value.

5. The body motion display device according to claim 2, wherein the display control part displays, on the display part, the number of kinds of body motion information according to the display characteristics of the display part.

6. The body motion display device according to claim 3, wherein the display control part displays, on the display part, the number of kinds of body motion information according to the display characteristics of the display part.

7. The body motion display device according to claim 4, wherein the display control part displays, on the display part, the number of kinds of body motion information according to the display characteristics of the display part.

8. The body motion display device according to claim 1, wherein the body motion information includes magnified images of the plurality of portions.

9. The body motion display device according to claim 2, wherein the body motion information includes magnified images of the plurality of portions.

10. The body motion display device according to claim 3, wherein the body motion information includes magnified images of the plurality of portions.

11. The body motion display device according to claim 4, wherein the body motion information includes magnified images of the plurality of portions.

12. The body motion display device according to claim 5, wherein the body motion information includes magnified images of the plurality of portions.

13. The body motion display device according to claim 8, wherein the display control part changes at least one of the display range of the magnified images and a magnification factor of the magnified images according to a region of the subject.

14. The body motion display device according to claim 8, wherein the display control part is part for changing at least one of the display range of the magnified images and a magnification factor of the magnified images according to the display characteristics of the display part.

15. The body motion display device according to claim 8, wherein the display control part displays, on the display part, a reference image, which is referred to for the determination of the presence or absence of body motion, along with the body motion information.

16. The body motion display device according to claim 9, wherein the display control part displays, on the display part, a reference image, which is referred to for the determination of the presence or absence of body motion, along with the body motion information.

17. The body motion display device according to claim 10, wherein the display control part displays, on the display part, a reference image, which is referred to for the determination of the presence or absence of body motion, along with the body motion information.

18. The body motion display device according to claim 1, wherein the display control part displays, on the display part, the body motion information for a portion in which an index value becoming a specific value is calculated.

19. The body motion display device according to claim 2, wherein the display control part displays, on the display part, the body motion information for a portion in which an index value becoming a specific value is calculated.

20. A body motion display method using the body motion display device according to claim 1 comprising:
   calculating an index value representing the degree of body motion of a subject included in a radiographic image in a plurality of portions on the radiographic image; and
   selectively displaying, on display part, at least one of a plurality of kinds of body motion information based on the index values in the plurality of portions.

21. The body motion display device according to claim 1, wherein the body motion appears as a shift in only one direction in the radiographic image.

22. The body motion display device according to claim 1, wherein the body motion does not include movement of organs.

23. The body motion display device according to claim 1, further comprising:
   a multiple resolution conversion unit for extracting a high-frequency component and a low-frequency component of the radiographic image.

24. The body motion display device according to claim 23, further comprising:
   a contrast calculation unit for calculating contrast of the high-frequency component and contrast of the low-frequency component.

25. The body motion display device according to claim 1, wherein the display control part selects the body motion information displayed on display part among the plurality of kinds of body motion information.

* * * * *